United States Patent [19]

Krogh

[11] Patent Number: 4,500,726

[45] Date of Patent: Feb. 19, 1985

[54] METHOD FOR PREPARING N-BENZYLOXYCARBONYL AMINO ACIDS CONTAINING ADDITIONAL FUNCTIONALITY

[75] Inventor: James A. Krogh, Mount Prospect, Ill.

[73] Assignee: PPG Industries, Inc., Pittsburgh, Pa.

[21] Appl. No.: 613,136

[22] Filed: May 23, 1984

[51] Int. Cl.³ .................................. C07C 125/065
[52] U.S. Cl. ........................ 56/160; 260/112.5 R; 548/533; 560/29; 560/148; 560/159
[58] Field of Search ............... 560/29, 148, 159, 160; 260/112.5 R; 548/533

[56] References Cited

U.S. PATENT DOCUMENTS

| | | | |
|---|---|---|---|
| 3,532,736 | 10/1970 | Chamberlin | 560/160 |
| 3,592,836 | 7/1971 | Ugi | 560/163 |
| 3,808,190 | 4/1974 | Dahlmans | 260/112.5 R |
| 3,875,207 | 4/1975 | Iselin | 560/160 |
| 4,033,998 | 7/1977 | Harris | 560/160 |
| 4,293,706 | 10/1981 | Gorman et al. | 560/163 |
| 4,345,091 | 8/1982 | Sugiyama | 560/163 |
| 4,450,284 | 5/1984 | Sathe | 560/163 |

OTHER PUBLICATIONS

McOmie, "Protective Groups in Organic Chemistry," pp. 56–60 (1973).
Greenstein, "Chemistry of the Amino Acids," vol. 2, pp. 887–901 (1961).
Bergmann, Ber., 65B, pp. 1192–1201 (1932).
D. M. Floyd et al, "Monobactams . . . " *Journal of Organic Chemistry* vol. 47, pp. 176–178 (1982).
C. M. Cimarusti et al., "Monobactams . . . " *Journal of Organic Chemistry* vol. 47, pp. 179–180 (1982).
Anon., "A New Generation of Antibiotics", *Science*, vol. 213, p. 1238 (1981).
E. Wertheim, *Textbook of Organic Chemistry*, 3d Edition, McGraw-Hill Book Co., Inc. New York, pp. 808–810 (1951).
H. Breuer et al., "Monocyclic β-Lactam Antibiotics . . . ", Abstract 878, 21st Interscience Conference on Antimicrobial Agents and Chemotherapy (1981).
Kimura and Regen, "Poly(Ethylene Glycols) and Poly-(Ethylene Glycol)–Grafted Copolymers . . . ", *Journal of Organic Chemistry*, vol. 48, No. 2, pp. 195–198 (1983).
Gokel, Goli, and Schultz, "Binding Profiles for Oligoethylene Glycols . . . ", *Journal of Organic Chemistry*, vol. 48, No. 17, pp. 2837–2842 (1983).
Kimura and Regen, "Poly(Ethylene Glycols) Are Extraordinary Catalysts . . . ", *Journal of Organic Chemistry*, vol. 47, No. 12, pp. 2493–2494 (1982).
Szabo, Aranyosi, and Toke, "Polyethylene Glycol Derivatives As Complexing Agents and Phase-Transfer Catalysts, IV," *Acta Chemica Scientiarum Hungaricae*, vol. 110, pp. 215–224 (1982).
R. A. Sawicki, "Phase Transfer Catalysts Polyethylene Glycols Immobilized Onto Metal Oxide Surfaces", *Tetrahedran Letters*, vol. 23, No. 22, pp. 2249–2252 (1982).
Heffernan, MacKenzie, and Sherrington, "Non-Supported and Resin-Supported Oligo(Oxyethylenes) . . . " *J.C.S. Perkin Transactions II*, pp. 514–517 (1981).
Zupancic and Kakalj, "Aromatic α,β-Unsaturated Nitriles Via Polyethylene Glycol-Catalyzed Two-Phase Aldol-Type Condensation", *Synthesis*, Nov. 1981, pp. 913–915.
Regen, Besse, and McLick, "Solid-Phase Cosolvents . . . ", *Journal of the American Chemical Society*, vol. 101, No. 1, pp. 116–120 (1979).
Balasubramanian, Sukumar, and Chandani, "Linear Unsubstituted Polyethylene Glycols as Phase Transfer Catalysts", *Tetrahedron Letters*, No. 37, pp. 3543–3544 (1979).
Yanagida et al, "Solid-Solid-Liquid Three Phase Transfer Catalysis . . . ", *Journal of Organic Chemistry*, vol. 44, No. 7, pp. 1099–1103 (1979).
Stott et al, "Modified Crown Ether Catalysts . . . ", *Journal of the American Chemical Society*, vol. 102, No. 14, pp. 4810–4815 (1980).
A. L. Lehninger, *Biochemistry*, 2d Ed., Worth Publishers, Inc., New York, pp. 71–83 (1975).

*Primary Examiner*—Michael L. Shippen
*Attorney, Agent, or Firm*—George D. Morris

[57] ABSTRACT

Poly(oxyalkylene) glycols and polymer-supported poly(oxyalkylene) alcohols are employed as phase-transfer reagents in blocking primary amino functionality of alkali metal salts of amino acids with a benzyloxycarbonyl group.

24 Claims, No Drawings

METHOD FOR PREPARING N-BENZYLOXYCARBONYL AMINO ACIDS CONTAINING ADDITIONAL FUNCTIONALITY

BACKGROUND OF THE INVENTION

Amino acids are often employed as raw materials in the preparation, by a sequence of reactions, of compounds having various uses. In many of these sequences it is necessary to reversibly block a primary amino group of the amino acid or its salts in order that the blocked compound may undergo further reactions which would otherwise irrevocably destroy the amino group, and yet permit later regeneration of the primary amino group.

Benzyloxycarbonyl is eminently suited as the blocking group for these purposes. See for example, U.S. Pat. No. 4,293,706, Floyd et al, "Monobactams...", *Journal of Organic Chemistry*, Vol. 47, No. 1, pages 176–178 (1982), Cimarusti et al, "Monobactams...", *Journal of Organic Chemistry*, Vol. 47, pages 179–180 (1982), and Wertheim, *Textbook of Organic Chemistry*, 3d edition, pages 808–809 (1951), the entire disclosures of which are incorporated herein by reference. The benzyloxycarbonyl group may be introduced by reacting alkali metal salt of the amino acid with a benzylhaloformate, such as benzylchloroformate or benzylbromoformate, in a polyphase reaction mixture.

When the amino acid contains, in addition to a primary amino group and at least one carboxylate anion, at least one functional group selected from the class consisting of hydroxyl, additional primary amino, secondary amino, primary imido, and primary amido, product yields are reduced due to the undesired side reaction of the benzylhaloformate with the additional functionality. A hydroxyl group, for instance, can and often does react with the benzylhaloformate to form an undesired carbonate. It is important to observe that loss of product by this mechanism pertains only to those amino acids containing the additional functionality; it does not pertain to those amino acids which do not contain the additional functionality.

Poly(oxyalkylene) glycols and polymer-supported poly(oxyalkylene) alcohols are known phase-transfer reagents which have been employed for various reactions. See, for example, Kimura and Regen, "Poly(ethylene glycols) and Poly(ethylene glycol)-Grafted Copolymers...", *Journal of Organic Chemistry*, Volume 48, No. 2, pages 195–198 (1983); Gokel, Goli, and Schultz, "Binding Profiles for Oligoethylene Glycols...", *Journal of Organic Chemistry*, Volume 48, No. 17, pages 2837–2842 (1983); Kimura and Regen, "Poly(ethylene glycols) Are Extraordinary Catalysts in Liquid-Liquid Two-Phase Dehydrohalogenation", *Journal of Organic Chemistry*, Volume 47, No. 12, pages 2493–2494 (1982); Szabo, Aranyosi, and Toke, "Polyethylene Glycol Derivatives As Complexing Agents and Phase-Transfer Catalysts, IV" *Acta Chemica Scientiarum Hungaricae*, Volume 110, pages 215–224 (1982); Sawicki, "Phase Transfer Catalysts. Polyethylene Glycols Immobilized onto Metal Oxide Surfaces", *Tetrahedron Letters* Volume 23, No. 22, pages 2249–2252 (1982); Heffernan, MacKenzie, and Sherrington, "Non-supported and Resin-supported Oligo (oxyethylenes) as Solid-Liquid Phase-transfer Catalysts. Effect of Chain Length and Head-group.", *J.C.S. Perkin Transactions* II, pp 514–517 (1981); Zupancic and Kokalj, "Aromatic $\alpha,\beta$-Unsaturated Nitriles via Polyethylene Glycol-Catalyzed Two-Phase Aldol-Type Condensation", *Synthesis*, November 1981, pages 913–915; Regen, Besse, and McLick, "Solid-Phase Cosolvents...", *Journal of the American Chemical Society*, Volume 101, No. 1, pages 116–120 (1979); and Balasubramanian, Sukumar, and Chandani, "Linear Unsubstituted Polyethylene Glycols as Phase Transfer Catalysts", *Tetrahedron Letters*, No. 37, pages 3543–3544 (1979), the entire disclosures of which are incorporated herein by reference. Neither the poly(oxyalkylene) glycols nor the polymer-supported poly(oxyalkylene) alcohols have, however, been employed as phase-transfer reagents in blocking a primary amino group of an amino acid having the additional functionality discussed above.

THE INVENTION

It has now been discovered that when a poly(oxyalkylene) glycol or a polymer-supported poly(oxyalkylene) alcohol is employed as a phase-transfer reagent in blocking a primary amino group of an alkali metal salt of an amino acid having the additional functionality heretofore described, the undesired side reaction of the benzylhaloformate with the additional functionality is greatly reduced. In other words, use of the poly(oxyalkylene) glycol or the polymer-supported poly(oxyalkylene) alcohol markedly and unexpectedly increases the specificity of the reaction producing the desired product. As a consequence, yields of the desired product are considerably increased. In the method, therefore, wherein alkali metal salt of an amino acid which is devoid of tertiary amino groups and quaternary ammonium groups, and which contains in addition to a primary amino group and at least one carboxylate anion, at least one functional group selected from the class consisting of hydroxyl, additional primary amino, secondary amino, primary imido, and primary amido, is reacted with benzylhaloformate selected from the group consisting of ring-substituted benzylchloroformate, ring-unsubstituted benzylchloroformate, ring-substituted benzylbromoformate, and ring-unsubstituted benzylbromoformate in a polyphase reaction mixture comprising an organic liquid phase and an aqueous liquid phase to produce alkali metal salt of an N-benzyloxycarbonyl amino acid in which the aromatic ring of the benzyl is substituted or unsubstituted and which contains the functional group, the invention is the improvement comprising conducting the reaciton in the presence of phase-transfer reagent comprising poly(oxyalkylene) glycol, polymer-supported poly(oxyalkylene) alcohol, or a mixture thereof.

Unless otherwise qualified or evident from its context, the nomenclature used herein for the various groups is without regard to whether they are protonated, neutral, or deprotonated.

Amino acids, the alkali metal salts of which are used as reactants in the present invention, are widely varied. They may be polypeptides of one, two, three, four, five, or more fundamental amino acid units, at least one of which contains the additional functionality described above. More usually, however, they are the fundamental amino acids themselves which contain the additional functionality. Examples include serine, threonine, tyrosine, lysine, arginine, 4-hydroxyproline, 5-hydroxylysine, $\epsilon$-N-methyllysine, homoserine, ornithine, canavanine, asparagine, glutamine, citrulline, and djenkolic acid. Fundamental amino acids containing hydroxyl functionality are preferred. Examples include serine, threonine, tyrosine, 4-hydroxyproline, 5-hydroxylysine, and homoserine.

The amino acids may individually have the L-configuration or the D-configuration, although the L-configuration is more common. Mixtures of amino acids, including racemic mixtures, may also be used.

The alkali metal salts of amino acids generally employed are those of lithium, sodium, or potassium. Ordinarily sodium or potassium is used. Sodium is preferred.

When substituted benzylchloroformate or substituted benzylbromoformate is employed as a reactant, the numbers and identities of the substituents are such that they do not render the benzylhaloformate unsuitable for its intended purpose. Examples of substituents which may be used include nitro, methyl, methoxy, chloro, and the like. While more than one substituent may be on the ring, and while the substituents may be the same or different, generally only one substituent is present, and this is often, but not necessarily, located in the 4-position. As between the substituted benzylchloroformates and the substituted benzylbromoformates, the former are more often used.

Unsubstituted benzylchloroformate and unsubstituted benzylbromoformate are preferred for use in the invention. Unsubstituted benzylchloroformate is especially preferred.

The poly(oxyalkylene) glycols and polymer-supported poly(oxyalkylene) alcohols most often employed as phase-transfer reagents in the present invention are represented by the formula

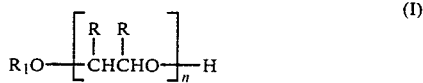

(I)

wherein
a. $R_1$ is hydrogen or a polymeric substrate,
b. one R of each individual —CH(R)CH(R)O— unit of the phase-transfer reagent is hydrogen or methyl, and the other R of the unit is hydrogen, methyl, or ethyl, and
c. the average value of n is at least about 4.

When the phase-transfer reagent of Formula I is an interpolymer of a plurality of alkylene oxides, the two R groups of some of the mer units will differ from those of other mer units. When the phase-transfer reagent is a homopolymer of one unsymmetrical alkylene oxide, as for example, propylene oxide or 1,2-butylene oxide, the two R groups of each mer unit will be different and they may be arranged regularly, irregularly or in block along the polymer, depending upon the manner in which the polymer was produced. When the phase-transfer reagent is a homopolymer of one symmetrical alkylene oxide, as for example, ethylene oxide or 2,3-butylene oxide, the two R groups of each mer unit will be the same.

Minor amounts of mer units other than CH(R)CH(R)O units may be present in the phase-transfer reagent so long as their identities and numbers do not seriously interfere with formation of the desired reaction product.

Polymer-supported poly(oxyalkylene) alcohols are known; see for example, Kimura and Regen (1983); Sawicki; Heffernan, MacKenzie, and Sherrington; and Regen, Besse, and McLick, cited above, and references cited therein. The polymeric substrate is usually organic, although it may be inorganic when the inorganic substrate and the poly(oxyalkylene) alcohol is bridged by a suitable coupling group such as a siloxane linkage or an oxy linkage. Typically the polymeric substrate is a polystyrene interpolymer. The polymeric substrate, whether organic or inorganic, serves to immobilize the poly(oxyalkylene) alcohol. In some applications this produces distinct advantages, including ease of removal of the phase-transfer reagent from liquid reaction mixtures as for example by filtration or centrifugation.

In Formula I, the value of n is generally in the range of from about 4 to about 500. Typically it is in the range of from about 4 to about 80. Preferably, the value of n is in the range of from about 5 to about 25.

In many cases, one R of each individual —CH(R)CH(R)O— unit is hydrogen and the other R of the unit is hydrogen or methyl.

The preferred phase-transfer reagents used in the present invention are those represented by the formula

(II)

where $R_1$ and n are as discussed with respect to Formula I.

When $R_1$ is hydrogen, Formula II represents the poly(ethylene glycols), also known as poly(oxyethylene) and as poly(ethylene oxide). The various poly(ethylene glycols) are often named in the format "PEG-number", where the number is the approximate number average molecular weight of the material.

The reaction of the alkali metal salt of the amino acid and the benzylhaloformate is conducted in a polyphase reaction mixture comprising an organic liquid phase and an aqueous liquid phase. In some instances, especially those in which the phase-transfer reagent is essentially insoluble in the liquid phases, a solid phase is also present.

The reaction may be carried out batchwise, continuously, semibatchwise, or semicontinuously.

Although extrinsic organic solvent is not ordinarily employed, it may be used when desired. Examples of suitable extrinsic organic solvents include benzene, toluene, xylene, chlorobenzene, nitrobenzene, pentane, hexane, heptane, petroleum ethers, tetrahydrofuran, diethyl ether, methylene chloride, chloroform, carbon tetrachloride, and 1,2-dichloroethane. Only one extrinsic organic solvent, a plurality of extrinsic solvents or no extrinsic organic solvent may be used. Usually, but not necessarily, the extrinsic solvent is inert under the conditions of the reaction.

The temperatures at which the reaction is conducted may vary considerably, but usually they are in the range of from about $-10°$ C. to about $+60°$ C. Temperatures in the range of from about $+5°$ C. to about $+30°$ C. are preferred.

The reaction is ordinarily conducted at or near ambient atmospheric pressure, although greater or lesser pressures may be used where desired.

The pH of the aqueous phase of the reaction mixture during the reaction is best discussed in terms of the $pK_2'$ value of the amino acid whose alkali metal salt is employed as a reactant. The $pK_2'$ values of amino acids and their determination are described by Lehninger, *Biochemistry*, 2d Edition, pages 71–81 (1975), the entire disclosure of which is incorporated herein by reference. Each amino acid has a characteristic $pK_2'$ value, and the $pK_2'$ values of the common amino acids are well established. See, for example, Lehninger, supra, and *The Merck Index*, 9th Edition (1976).

The pH of the aqueous phase of the reaction mixture during the reaction may vary considerably, but usually the pH is in the range of from about ($pK_2'-2$) to about ($pK_2'+2$). Often the pH is in the range of from about ($pK_2'-1.5$) to about ($pK_2'+1.5$). Typically the pH is in the range of from about $pK_2'$ to about ($pK_2'+1.5$). From about $pK_2'$ to about ($pK_2'+1$) is preferred.

The reaction is conducted by admixing the benzylhaloformate, an aqueous solution of the alkali metal salt of the amino acid, and the phase-transfer reagent while maintaining the pH of the aqueous phase in the desired range. Ordinarily, but not necessarily, the phase-transfer reagent is admixed with the aqueous solution and then the benzylhaloformate is added while the pH of the aqueous phase is maintained by the generally concurrent addition of aqueous alkali metal hydroxide solution as a separate stream. After completing the addition of benzylhaloformate to the reaction mixture, agitation and addition of aqueous alkali metal hydroxide are continued until essentially complete reaction of the benzylhaloformate occurs as indicated by stabilization of the pH. Stabilization of pH is indicated when no additional alkali metal hydroxide is required to be added to the reaction mixture to maintain the pH within the desired range.

The molar ratio of the benzylhaloformate to the alkali metal salt of the amino acid ultimately employed may vary considerably, but usually it is in the range of from about 0.9:1 to about 1.3:1. Often molar ratio is in the range of from about 1:1 to about 1.2:1. Preferably it is in the range of from about 1:1 to about 1.05:1.

The equivalent ratio of the phase-transfer reagent to the alkali metal salt of the amino acid ultimately employed may also vary considerably. Typically the equivalent ratio is in the range of from about 0.001:1 to about 0.1:1. Often the equivalent ratio is in the range of from about 0.001:1 to about 0.01:1. From about 0.002:1 to about 0.005:1 is preferred.

The product of the reaction, namely, alkali metal salt of an N-benzyloxycarbonyl amino acid, may be recovered from the reaction mixture when this is desired. More commonly, however, the reaction mixture is acidified, usually with cooling, to convert the product to the free amino acid. Examples of acids that can be used for the acidification include hydrochloric acid, hydrobromic acid, sulfuric acid, nitric acid, phosphoric acid, boric acid, and acetic acid. It is preferred to use the hydrohalic acid corresponding to the benzylhaloformate originally employed so as not to introduce a further anionic species to the reaction mixture. Acidification can be conducted to any desired pH, but ordinarily the final pH of the reaction mixture is in the range of from about 1 to about 4. Preferably the final pH is in the range of from about 1.5 to about 3. In most instances as the acidification progresses, a pH is reached where the N-benzyloxycarbonyl amino acid begins to precipitate. Continued acidification then results in further precipitation until the reaction mixture is nearly exhausted of amino acid.

The temperatures at which acidification may be conducted may vary considerably, but usually they are in the range of from about $-10°$ C. to about $+60°$ C. Temperatures in the range of from about $+5°$ C. to about $+20°$ C. are preferred.

The acidification is ordinarily conducted at or near ambient atmospheric pressure, although greater or lesser pressures may be used where desired.

The precipitated amino acid may be separated from its mother liquor by conventional procedures such as decantation, filtration, or centrifugation. In a preferred embodiment, however, the precipitate is dissolved by adding an organic solvent, such as for example, ethyl acetate, diethyl ether, toluene, tetrahydrofuran, or bis(2-methoxyethyl)ether, to the reaction mixture. After the organic and aqueous phases have been separated, the N-benzyloxycarbonyl amino acid may be recovered by any conventional procedure, as for example, by solvent-stripping and drying.

The poly(ethylene glycols) possess several advantages over the crown ethers and silacrown ethers when used as phase-transfer reagents in preparing N-blocked amino acids. Among these are lower cost, greater availability, and the greater likelihood that the poly(ethylene glycol) will remain in the aqueous phase upon extraction than the crown ethers or silacrown ethers of similar molecular weight.

The N-benzyloxycarbonyl amino acids produced by the process of the present invention have many and varied uses. They may, for example, be used in the preparation of polypeptides by the Bergman method. Many of them, as for example, N-benzyloxycarbonyl-L-threonine and N-benzyloxycarbonyl-L-serine, may be used in the preparation of monocyclic $\beta$-lactam antibiotics, commonly known as monobactams.

When further reaction products have been produced from the N-benzyloxycarbonyl amino acid or alkali metal salt thereof, the benzyloxycarbonyl group may be removed to restore the original primary amino functionality. This is usually accomplished by catalytic hydrogenation or sometimes by hydrolysis.

The invention is further described in conjunction with the following examples which are to be considered illustrative rather than limiting, and in which all parts are parts by weight and all percentages are percentages by weight unless otherwise specified.

EXAMPLE I

This is a comparative example showing the effect of using no phase transfer catalyst in the preparation of N-benzyloxycarbonyl-L-threonine.

A 2-liter, 5-necked reaction flask equipped with a thermometer, a mechanical agitator, a pH electrode, and two constant-volume addition funnels was charged with 119.2 grams of L-threonine (98%) and 600 grams of water. Eighty grams of 50% aqueous sodium hydroxide solution was then added to convert the amino acid to the sodium salt. The reaction mixture then had a pH of about 11.3. The additions of 174.0 grams of benzylchloroformate (99%; hereinafter "BCF"), 80 grams of 50% aqueous sodium hydroxide solution (hereinafter "caustic solution") and concentrated hydrochloric acid (hereinafter "HCl acid") as separate streams were accomplished according to Table 1.

TABLE 1

| Time, Hours:minutes | Temperature, °C. | pH | Remarks |
|---|---|---|---|
| 0:00 | 14 | 11.3 | BCF addition begun. |
| 0:05 | 16 | 11.1 | Addition of caustic solution begun. |
| 0:15 | 17 | 10.9 | About ¼ BCF added. |
| 0:25 | 18 | 10.8 | |
| 0:34 | 18 | 10.9 | About ½ BCF added. |
| 0:45 | 15 | 11.2 | |
| 0:50 | 14 | 11.4 | About ¾ BCF added. |
| 1:00 | 17 | 11.2 | |

TABLE 1-continued

| Time, Hours:minutes | Temperature, °C | pH | Remarks |
|---|---|---|---|
| 1:10 | 16 | 11.3 | BCF addition complete. |
| 1:27 | 15 | 11.0 | Addition of caustic solution completed. |
| 1:29 | 16 | 11.0 | pH had stabilized. |
| 1:40 | 16 | 11.0 | HCl acid addition begun. |
| 2:03 | 13 | 1.7 | Intermittent HCl acid addition continued. |
| 2:25 | 14 | 1.7 | HCl acid addition completed; pH had stabilized. |

The amount of hydrochloric acid used was that necessary to reduce the pH to a stabilized value of 1.7. During the hydrochloric acid addition, a precipitate suddenly began to form at about pH 4.0, which froze into a near-solid mixture stopping the agitator. Approximately 600 cubic centimeters of ethyl acetate was added and the agitator was manually turned until it could move slowly under its own power. As the reaction mixture was stirred, the precipitate dissolved and permitted the agitator to move freely. After the pH had stabilized at 1.7, stirring was continued for about 15 minutes and then discontinued. The reaction mixture was then charged into a 2-liter separatory funnel and the phases allowed to separate. The bottom aqueous phase was drained off and reextracted with a further 300 cubic centimeters of ethyl acetate. The phases were separated and the organic phases from both extractions were combined and stored overnight over anhydrous magnesium sulfate. The solid phase was then removed by filtration and the filtrate was stripped in a Buchi rotary evaporator at about 40° C. and under the vacuum provided by a water aspirator. The solids were dried for 4 hours in a vacuum oven at about 45° C. and absolute pressures in the range of from about 3 to about 17 kilopascals, and then placed in a vacuum desiccator over phosphorous pentoxide for 16 hours at ambient temperature an absolute pressure of about 13 to 27 pascals. The resulting product weighed 210.20 grams and melted in the range of 93° to 95° C. The yield of product was 83.0%, based on L-threonine. Nuclear magnetic resonance spectroscopy showed no moisture to be present. Analysis for purity was run by titration. Purity Found: 99.6%. The product was analyzed for NaCl. Found: 0.27% NaCl. The product was analyzed for moisture. Found: 0.31% $H_2O$. Four-tenths of a gram of the product was dissolved in 10 milliliters of acetic acid and the specific rotation $[\alpha]_D^{20}$ was determined. Found: $-3.67°$. Liquid chromatograhy showed the product to contain 99.9 area percent benzyloxycarbonyl-L-threonine when measured at 254 nanometers and 96.3 area percent N-benzyloxycarbonyl-L-threonine when measured at 210 nanometers. The infrared spectrum of the product matched the standard spectrum for N-benzyloxycarbonyl-L-threonine. The nuclear magnetic resonance spectrum of the product matched the standard spectrum for N-benzyloxycarbonyl-L-threonine, except that the former also indicated the presence of traces of an undefined impurity. The results of elemental analysis are shown in Table 2.

TABLE 2

|  | % C | % H | % N | % O |
|---|---|---|---|---|
| Found | 56.83 | 6.03 | 5.44 | 31.56 |
|  | 56.78 | 6.10 | 5.49 | 31.45 |
| Average Found | 56.81 | 6.07 | 5.47 | 31.51 |
| Theory | 56.91 | 5.97 | 5.53 | 31.59 |

The product appeared to be of analytical purity with all values in very good agreement.

EXAMPLE II

This example shows the effect of using PEG-600 as a phase transfer catalyst in the preparation of N-benzyloxycarbonyl-L-threonine.

A 1-liter, 5-necked reaction flask equipped as in Example I was charged with 59.56 grams of L-threonine (98%) and 300 grams of water. Forty grams of 50% aqueous sodium hydroxide solution was then added to convert the amino acid to the sodium salt. The reaction mixture then had a pH of about 11.0. To the reaction mixture was added 1.5 grams of PEG-600; no change in pH was observed. The additions of 87.0 grams of benzylchloroformate ("BCF") and 40 grams of 50% aqueous sodium hydroxide solution ("caustic") as separate streams were accomplished according to Table 3.

Concentrated hydrochloric acid was charged to the addition funnel that had contained the benzylchloroformate. After cooling the reaction mixture to about 10° C. with an ice bath, the pH was reduced to about 1.5 by the dropwise addition of concentrated hydrochloric acid with cooling over a period of about 20 minutes.

TABLE 3

| Time, hours:minutes | Temperature, °C | pH | Volume BCF in Addition Funnel, cm³, approximate | Volume Caustic in Addition Funnel, cm³, approximate | Remarks |
|---|---|---|---|---|---|
| 0:00 | 16 | 11.0 | 70 | 27 | BCF addition begun. |
| 0:02 | 15 | 11.0 | 67 | 27 | Slight pH decrease; caustic addition begun. |
| 0:05 | 15 | 10.9 | 62 | 26.5 | Began chilling vessel with ice bath. |
| 0:10 | 16 | 10.8 | 58 | 25 |  |
| 0:15 | 15 | 10.7 | 54 | 24 |  |
| 0:25 | 14 | 10.8 | 43 | 20 |  |
| 0:32 | 12 | 10.9 | 35 | 16 | Ice bath Removed. |
| 0:40 | 14 | 10.7 | 30 | 12 |  |
| 0:45 | 15 | 11.2 | 26 | 10 |  |
| 0:50 | 18 | 11.0 | 23 | 8 | Began chilling vessel with ice bath. |
| 0:55 | 13 | 11.3 | 20 | 7 | Ice bath removed. |
| 0:57 | 15 | 10.9 | 17 | 6.5 |  |
| 1:00 | 16 | 10.8 | 14 | 5 | Began chilling |

TABLE 3-continued

| Time, hours:minutes | Temperature, °C. | pH | Volume BCF in Addition Funnel, cm³, approximate | Volume Caustic in Addition Funnel, cm³, approximate | Remarks |
| --- | --- | --- | --- | --- | --- |
| | | | | | vessel with ice bath. |
| 1:05 | 16 | 11.1 | 9 | 4 | |
| 1:15 | 15 | 11.0 | 0 | 0 | Both additions completed within same minute; ice bath removed. |
| 1:17 | 16 | 11.0 | 0 | 0 | pH is essentially stable; added two drops of caustic. |
| 1:20 | 16 | 11.1 | 0 | 0 | pH is stable. |
| 1:50 | 17 | 11.1 | 0 | 0 | pH is stable. |

When the pH reached about 4.5, a milky white precipitate began to form. After the pH had reached about 1.5, the addition was stopped. The pH rose slowly to about 2.2 over a period of about 15 minutes and stabilized at that value. The precipitate remained after the pH of the reaction mixture had stabilized at about 2.2. Though milky, no solids were visible even after allowing the reaction mixture to stand quiescently for a time. Stirring was resumed and concentrated hydrochloric acid was added dropwise until the pH of the reaction mixture had reached about 1.5. The reaction mixture was then stirred for about 20 minutes during which time the pH remained at about 1.5. At the conclusion of this time, 200 cubic centimeters of ethyl acetate was added, whereupon all solids dissolved. The reaction mixture was agitated strongly for about 10 minutes and then stirring was discontinued. The upper organic layer separated very cleanly from the lower aqueous layer after about 2 to 3 minutes. The reaction mixture was then charged into a one liter separatory funnel and the phases allowed to separate. The lower aqueous layer was drawn off and reextracted with 100 cubic centimeters of fresh ethyl acetate. After removal of the aqueous phase, the two organic phases were combined. The solvent was stripped in a Buchi rotating evaporator under the vacuum provided by a water aspirator (absolute pressure: about 9 to 10 kPa), first using a 50° to 55° C. water bath until all solids had formed, and then using a 60° C. water bath for one hour of slow rotation. The vacuum was released and the solids were charged to a drying tray and heated in a convection oven at 50° C. to 55° C. overnight. The solids were powdered by emaciation in a blender, placed on the drying tray, and dried in the convection oven for about 6¼ hours. The resulting product weighed 120.5 grams and represented a yield of 95.16%, based on L-threonine. Analysis for purity was run by dissolving a sample of the product in water and titrating with a sodium hydroxide/methanol solution. Purity Found: 96.89%, 97.23%, 97.15%. Average Purity Found: 97.09%. The product was analyzed for NaCl. Found: 0.14%, 0.14% NaCl. Average Found: 0.14% NaCl. The product was analyzed for moisture by the Karl Fischer method. Found: 0.046%, 0.053% $H_2O$. Average Found: 0.050% $H_2O$. Four-tenths of a gram of the product was dissolved in 10 milliliters of acetic acid and the specific rotation was determined. Found: −3.80°, −3.88°. Average Found: −3.84°. Liquid chromatography showed the product to contain 98.843 area percent N-benzyloxycarbonyl-L-threonine and 0.102 area percent L-threonine when measured at 210 nanometers. The nuclear magnetic resonance spectrum of the product precisely matched the literature spectrum of N-benzyloxycarbonyl-L-threonine. The results of elemental analysis are shown in Table 4.

TABLE 4

| | % C | % H | % N | % O |
| --- | --- | --- | --- | --- |
| Found | 56.95 | 5.91 | 5.49 | 31.60 |
| | 57.09 | 6.07 | 5.58 | 31.27 |
| Average Found | 57.02 | 5.99 | 5.54 | 31.44 |

This example shows about a 14½% increase in yield as compared to the yield of Example I, and that PEG-600 effectively catalyzed the reaction.

EXAMPLE III

This example shows the effect of using PEG-300 as a phase transfer catalyst in the preparation of N-benzyloxycarbonyl-L-threonine.

A 1-liter, 5-necked reaction flask equipped as in Example I was charged with 59.56 grams of L-threonine and 300 grams of water. Forty grams of 50% aqueous sodium hydroxide solution was then added to convert the amino acid to the sodium salt. The reaction mixture then had a pH of 11.1. To the reaction mixture was added 0.75 gram of PEG-300; no change in pH was observed. The additions of 87.0 grams of benzylchloroformate ("BCF") and 40 grams of 50% aqueous sodium hydroxide solution ("caustic") as separate streams were accomplished according to Table 5.

Concentrated hydrochloric acid was charged to the addition funnel that had contained the benzylchloroformate. While cooling the reaction vessel with an ice bath such that the temperature of the reaction was maintained in the range from 5° C. to 10° C., the pH was reduced to 1.5 by the dropwise addition of concentrated hydrochloric acid over a period of about 20 minutes. When the pH reached about 4.5, a milky white precipitate began to form. After the pH had reached about 1.5, the addition was stopped. The pH rose slowly to about 2.1 over a period of about 15 minutes. A few drops of concentrated hydrochloric acid were added to return the pH to about 1.5. The precipitate remained after the pH had been returned to a value of about 1.5. Although the reaction mixture is a somewhat viscous slurry, no individual crystals were visible. The reaction mixture was stirred for an additional 30 minutes while allowing it to return to ambient temperature. At the conclusion of this time, 200 cubic centimeters of ethyl acetate was added, whereupon all solids dissolved. The reaction mixture was stirred for 5 minutes and then charged to a one-liter separatory funnel where the phases were allowed to separate. After two or three minutes, the phases had separated cleanly into two very well defined layers. The lower aqueous layer was drawn off and reextracted with 100 cubic centimeters of fresh ethyl acetate.

liquid chromatography showed the product to contain 96.824 area percent N-benzyloxycarbonyl-L-threonine, 0.897 area percent benzyl alcohol, and 0.283 area per-

TABLE 5

| Time, hours:minutes | Temperature, °C. | pH | Volume BCF in Addition Funnel, cm³, approximate | Volume Caustic in Addition Funnel, cm³, approximate | Remarks |
|---|---|---|---|---|---|
| 0:00 | 15 | 11.1 | 71 | 27 | BCF addition begun. |
| 0:03 | 15 | 11.05 | 70 | 27 | Slight pH drop began. |
| 0:05 | 15 | 11.0 | 68 | 27 | Caustic addition begun. |
| 0:11 | 16 | 11.0 | 52 | 25 | Began chilling vessel with ice bath; slowed rate of BCF addition slightly. |
| 0:18 | 17 | 10.8 | 47 | 23.5 | |
| 0:22 | 15 | 10.9 | 45 | 22.5 | |
| 0:27 | 14 | 10.9 | 41 | 20.5 | Ice bath Removed. |
| 0:32 | 17 | 10.9 | 38 | 18 | Began chilling vessel with ice bath. |
| 0:35 | 16 | 10.9 | 35.5 | 17 | |
| 0:42 | 16 | 11.1 | 30 | 12 | |
| 0:47 | 16 | 11.0 | 25 | 10 | |
| 0:52 | 15 | 10.7 | 19 | 8 | |
| 0:57 | 15 | 11.0 | 15 | 7 | |
| 1:02 | 15 | 10.9 | 9 | 4.5 | |
| 1:07 | 15 | 10.9 | 5 | 2 | |
| 1:12 | 15 | 11.1 | 0 | 0 | Both additions completed; two additional drops of caustic were added; ice bath removed. |
| 1:17 | 17 | 11.2 | 0 | 0 | |
| 1:19 | 17 | 11.2 | 0 | 0 | pH is stable. |
| 1:27 | 18 | 11.2 | 0 | 0 | pH is stable. |
| 2:27 | 23 | 11.2 | 0 | 0 | pH is stable. |

After removal of the lower aqueous phase, the two organic phases were combined. The solvent was stripped over a period of about 2 hours in a Buchi rotating evaporator under the vacuum provided by a water aspirator (absolute pressure: about 9 to 10 kPa), using a water bath ultimately reaching 60° C. The vacuum was released and the solids were scraped from the side of the flask. Once the solids were loosened and free flowing, evaporation was continued in the Buchi evaporator for one hour under the vacuum provided by a water aspirator and using a 55° C. water bath. The vacuum was released and the solids were placed in a drying dish. The solids were then dried overnight in a convection oven at 50° C. to 55° C. The solids were pulverized in a blender, placed in a drying dish, and dried in the convection oven over the weekend. The resulting product weighed 120.0 grams and represented a yield of 94.76%, based on L-threonine. Analysis for purity was run by dissolving a sample of the product in water and titrating with a sodium hydroxide/methanol solution. Purity Found: 96.95%, 97.38%. Average Purity Found: 97.16%. The product was analyzed for NaCl. Found: 0.074%, 0.099% NaCl. Average Found: 0.087% NaCl. The product was analyzed for moisture by the Karl Fischer method. Found 0.12%, 0.08% $H_2O$. Average Found: 0.10% $H_2O$. Four-tenths of a gram of the product was dissolved in 10 milliliters of acetic acid and the specific rotation was determined. Found: −3.82°, −3.46°. Average Found: −3.64°. The product melted in the range of from 97° C. to 99° C. Liquid chromatography showed the product to contain 100 area percent N-benzyloxycarbonyl-L-threonine when measured at 254 nanometers. When measured at 210 nanometers, cent L-threonine. The nuclear magnetic resonance spectrum of the product matched the standard spectrum of N-benzyloxycarbonyl-L-threonine. The results of elemental analysis are shown in Table 6.

TABLE 6

| | % C | % H | % N | % O |
|---|---|---|---|---|
| Found | 56.87 | 5.94 | 5.34 | 31.37 |
| | 56.91 | 6.06 | 5.61 | 31.28 |
| Average Found | 56.89 | 6.00 | 5.48 | 5.53 |

This example shows about a 14% increase in yield as compared to the yield of Example I, and that PEG-300 effectively catalyzed the reaction.

EXAMPLE IV

This example shows the effect of using about half the amount of PEG-300 as was used in Example III.

A 1-liter, 5-necked reaction flask equipped as in Example I was charged with 59.56 grams of L-threonine and 300 grams of water. Forty grams of 50% aqueous sodium hydroxide solution was then added to convert the amino acid to the sodium salt. The reaction mixture then had a pH of 11.2. To the reaction mixture was added 0.38 gram of PEG-300; no change in pH was observed. The additions of 87.0 grams of benzylchloroformate ("BCF") and 40 grams of 50% aqueous sodium hydroxide solution ("caustic") as separate streams were accomplished according to Table 7.

Concentrated hydrochloric acid was charged to the addition funnel that had contained the benzylchloroformate.

TABLE 7

| Time, hours:minutes | Temperature, °C. | pH | Volume BCF in Addition Funnel, cm³, approximate | Volume Caustic in Addition Funnel, cm³, approximate | Remarks |
|---|---|---|---|---|---|
| 0:00 | 16 | 11.2 | 71 | 27 | BCF addition begun. |
| 0:01 | 16 | 11.15 | 70.5 | 27 | Slight pH drop began. |
| 0:04 | 16 | 11.0 | 68 | 27 | Caustic addition begun. |
| 0:09 | 17 | 10.9 | 63 | 26 | Began chilling vessel with ice bath; |
| 0:14 | 15 | 10.8 | 59 | 24 | |
| 0:19 | 16 | 11.0 | 54 | 22 | |
| 0:24 | 15 | 10.8 | 49 | 20 | |
| 0:29 | 14 | 10.8 | 45 | 18 | |
| 0:34 | 13 | 11.1 | 41 | 16 | Ice bath partially removed. |
| 0:39 | 15 | 10.9 | 36 | 14 | |
| 0:44 | 16 | 11.2 | 31 | 12 | |
| 0:49 | 17 | 11.0 | 25 | 9 | |
| 0:54 | 16 | 10.8 | 20 | 7 | Increased cooling. |
| 0:59 | 15 | 10.7 | 15 | 6 | |
| 1:04 | 15 | 10.9 | 9 | 4 | |
| 1:09 | 16 | 11.1 | 4 | 2 | |
| 1:14 | 16 | 11.0 | 0 | 0 | Both additions completed. |
| 1:15 | 16 | 10.8 | 0 | 0 | Added a few drops of caustic; ice bath removed. |
| 1:21 | 17 | 11.0 | 0 | 0 | pH essentially stable. |
| 2:39 | 20 | 10.9 | 0 | 0 | pH essentially stable. |

After cooling the reaction mixture to about 10° C. using an ice bath, the pH was reduced to about 1.5 by the dropwise addition of concentrated hydrochloric acid over a period of about 20 minutes while cooling with an ice bath to maintain the temperature in the range of from about 5° to about 10° C. When the pH reached about 4.5, a milky white precipitate began to form. After the pH had reached about 1.5, the addition was stopped. The pH rose slowly to about 2.1. A few drops of concentrated hydrochloric acid were added to return the pH to about 1.5. The reaction mixture was then stirred while allowing it to return to ambient temperature. About 200 cubic centimeters of ethyl acetate was then added, whereupon all solids dissolved. The reaction mixture was stirred and then charged to a one-liter separatory funnel where the phases were allowed to separate. The lower aqueous layer was drawn off and reextracted with about 100 cubic centimeters of fresh ethyl acetate. After removal of the lower aqueous phase, the two organic phases were combined. The solvent was stripped in a Buchi rotating evaporator under the vacuum provided by a water aspirator (absolute pressure: about 9 to 10 kPa), using a warm water bath ultimately reaching about 55° C. As ethyl acetate was removed, a viscous clear syrup formed, the syrup whitened, and a precipitate formed which coated the flask. The vacuum was released and the solids were scraped from the side of the flask. Once the solids were loosened and free flowing, evaporation was continued in the Buchi evaporator for one hour under the vacuum provided by a water aspirator using a warm water bath. The vacuum was released and the solids were placed in a drying dish. The solids were dried in a convection oven at 55° C. over the weekend. The solids were pulverized to a fine powder in a blender, placed in a drying dish, and dried in the convection oven for 3 hours at 50° C. to 55° C. The resulting product weighed 114.09 grams and represented a yield of 90.1%, based on L-threonine. Analysis for purity was run by dissolving a sample of the product in water and titrating with a sodium hydroxide/methanol solution. tion. Purity Found: 94.47%, 94.15%. Average Purity Found: 94.31%. The product was analyzed for NaCl. Found: 0.33%, 0.36% NaCl. Average Found: 0.34% NaCl. The product was analyzed for moisture by the Karl Fischer method. Found: 0.21%, 0.18% H$_2$O. Average Found: 0.20% H$_2$O. Four-tenths of a gram of the product was dissolved in 10 milliliters of acetic acid and the specific rotation was determined. Found: −3.69°, −3.04°. Average Found: −3.36°. Liquid chromatography showed the product to contain 97.7 area percent N-benzyloxycarbonyl-L-threonine when measured at 210 nanometers and 97.92 area percent N-benzyloxycarbonyl-L-threonine when measured at 254 nanometers. The nuclear magnetic resonance spectrum of the product matched the standard spectrum of N-benzyloxycarbonyl-L-threonine.

This example shows about an 8½% increase in yield as compared to the yield of Example I, and that PEG-300 effectively catalyzed the reaction.

EXAMPLE V

This example shows the effect of using tetra(ethylene glycol) as a phase transfer catalyst in the preparation of N-benzyloxycarbonyl-L-threonine.

A 1-liter, 5-necked reaction flask equipped as in Example I was charged with 59.56 grams of L-threonine and 300 grams of water. Forty grams of 50% aqueous sodium hydroxide solution was then added to convert the amino acid to the sodium salt. The reaction mixture then had a pH of 11.18. To the reaction mixture was added 0.49 gram of tetra(ethylene glycol); no change in pH was observed. The additions of 87.0 grams of benzylchloroformate ("BCF") and 40 grams of 50% aqueous sodium hydroxide solution ("caustic") as separate streams were accomplished according to Table 8.

Concentrated hydrochloric acid was charged to the addition funnel that had contained the benzylchloroformate. After cooling the reaction mixture to about 10° C. using an ice bath, the pH was reduced to about 1.5 by the dropwise addition of concentrated hydrochloric acid over a period of about 20 minutes while cooling with an ice bath to maintain the temperature in the range of from about 5° C. to about 10° C. When the pH reached about 4.5, a milky white precipitate began to form. After the pH had reached about 1.5, the addition was stopped. The pH rose slowly to about 2.1 over a period of about 15 minutes. A few drops of concentrated hydrochloric acid were added to return the pH to about 1.5. The reaction mixture was then stirred about 20 minutes, during which time a drop or two of concentrated hydrochloric acid was added as necessary to maintain the pH below about 1.8. The pH stabilized at about 1.7. Stirring and cooling were continued for about 20 minutes, when the entire reaction mixture abruptyly crystallized to a solid mass. The temperature was about 7° C. when the abrupt crystallization occurred. Stirring was discontinued and about 200 cubic centimeters of ethyl acetate was added. The stirrer was moved manually until sufficient solids had dissolved to permit the stirrer to rotate. A couple of minutes of agitation was sufficient to dissolve all the solids. The reaction mixture was then stirred vigorously for 5 minutes and then charged to a one-liter separatory funnel where the phases were allowed to separate. After two or three minutes, the phases had separated into well defined layers. The lower aqueous layer was drawn off and reextracted with about 100 cubic centimeters of fresh ethyl acetate. After removal of the lower aqueous phase, the two organic phases were combined.

TABLE 8

| Time, hours:minutes | Temperature, °C. | pH | Volume BCF in Addition Funnel, $cm^3$, approximate | Volume Caustic in Addition Funnel, $cm^3$, approximate | Remarks |
|---|---|---|---|---|---|
| 0:00 | 13 | 11.2 | 71 | 28 | BCF addition begun. |
| 0:01 | 13 | 11.15 | 70 | 28 | Slight pH drop began. |
| 0:03 | 14 | 11.1 | 68.5 | 28 | Caustic addition begun. |
| 0:10 | 14 | 11.0 | 62.5 | 27.5 | |
| 0:15 | 16 | 10.8 | 59.5 | 26.5 | Began chilling vessel with ice bath. |
| 0:20 | 14 | 11.2 | 57 | 25.5 | Addition rates increased slightly. |
| 0:27 | 14 | 11.1 | 53 | 24 | Ice bath Removed. |
| 0:32 | 15 | 10.9 | 48 | 23 | |
| 0:37 | 16 | 11.1 | 44 | 20 | Began chilling vessel with ice bath. |
| 0:42 | 13 | 10.8 | 39 | 18 | Ice bath partially removed. |
| 0:47 | 15 | 10.9 | 35 | 16 | |
| 0:52 | 15 | 11.2 | 29 | 14 | |
| 1:07 | 15 | 11.0 | 19 | 8 | |
| 1:12 | 17 | 11.1 | 12 | 6 | Contact of vessel with ice bath increased. |
| 1:17 | 16 | 11.1 | 5 | 2.5 | |
| 1:21 | 14 | 11.2 | 0 | 0 | Both additions completed. |
| 1:23 | 13 | 11.2 | 0 | 0 | pH essentially stabilized; added two drops of caustic. |
| 1:26 | 14 | 11.2 | 0 | 0 | pH essentially stable; ice bath removed. |
| 1:42 | 16 | 11.2 | 0 | 0 | pH is stable. |
| 2:32 | 21 | 11.2 | 0 | 0 | pH is stable. |

The solvent was stripped in a Buchi rotating evaporator under the vacuum provided by a water aspirator (absolute pressure: about 9 to 10 kPa) using a water bath ultimately reaching 60° C. As ethyl acetate was removed, a viscous clear syrup formed, the syrup whitened, and a precipitate formed which coated the flask. The vacuum was released and the solids were scraped from the side of the flask. Once the solids were loosened and free flowing, evaporation was continued in the Buchi evaporator for one hour under the vacuum provided by a water aspirator using a warm water bath. The vacuum was released and the solids were placed in a drying dish. The solids were then dried overnight in a convection oven at 55° C. The solids were pulverized to a powder in a blender, placed in a drying dish, and dried in the convection oven for 6 hours. The resulting product weighed 119.0 grams and represented a yield of 94.0%, based on L-threonine. Analysis for purity was run by dissolving a sample of the product in water and titrating with a sodium hydroxide/methanol solution. Purity Found: 95.90%, 95.65%. Average Purity Found: 95.78%. The product was analyzed for NaCl. Found: 0.41%, 0.40% NaCl. Average Found: 0.41% NaCl. The product was analyzed for moisture by the Karl Fischer method. Found: 0.03%, 0.06% $H_2O$. Average Found: 0.05% $H_2O$. Four-tenths of a gram of the product was dissolved in 10 milliliters of acetic acid and the specific rotation was determined. Found: −3.90°, −3.71°. Average Found: −3.80°. Liquid chromatography showed the product to contain 97.8 area percent N-benzyloxycarbonyl-L-threonine when measured at 210 nanometers and 98.53 area percent N-benzyloxycarbonyl-L-threonine when measured at 254 nanometers. The nuclear magnetic resonance spectrum of the product matched the standard spectrum of N-benzyloxycarbonyl-L-threonine.

This example shows about a 13% increase in yield as compared to the yield of Example I, and that tetra(ethylene glycol) effectively catalyzed the reaction.

EXAMPLE VI

This is a comparative example showing the effect of using no phase transfer catalyst in the preparation of N-benzyloxycarbonyl-L-serine.

A 1-liter, 5-necked reaction flask equipped as in Example I was charged with 42.04 grams of L-serine and 211 cubic centimeters of water. Thirty-two grams of 50% aqueous sodium hydroxide solution was then added dropwise over a period of about 10 minutes to convert the amino acid to the sodium salt. The reaction mixture then had a pH of about 11.1. The additions of 69.43 grams of benzylchloroformate (hereinafter "BCF") and about 32 grams of 50% aqueous sodium hydroxide solution (hereinafter "caustic solution") as separate streams were accomplished according to Table 9.

TABLE 9

| Time, Hours: minutes | Temperature, °C. | pH | Remarks |
|---|---|---|---|
| 0:00 | 12 | 11.1 | BCF addition begun. |
| 0:03 | 13 | 10.9 | Addition of caustic solution begun. |
| 0:10 | 16 | 10.8 | |
| 0:15 | 17 | 10.7 | |
| 0:20 | 21 | 11.5 | Cooling applied. |
| 0:25 | 18 | 11.1 | |
| 0:30 | 17 | 11.2 | |
| 0:35 | 15 | 11.1 | |
| 0:40 | 14 | 10.8 | |
| 0:45 | 14 | 10.9 | BCF addition completed. Continued adding a few cubic centimeters of caustic solution and then stopped the addition. |
| 0:50 | 13 | 9.8 | Added about 2 cubic centimeters of caustic solution to raise pH to 11.0. |
| 1:05 | 13 | 11.1 | pH has essentially stabilized. |

The reaction mixture was then stirred at a pH of about 11.0 for 30 minutes. After cooling the reaction mixture to about 10° C., the pH was reduced to about 1.5 by the dropwise addition of concentrated hydrochloric acid with cooling over a period of about 15 minutes. A precipitate began to form between pH 6.1 and pH 5.5. Upon completion of the hydrochloric acid addition, the reaction mixture was stirred for 30 minutes and then left to stand overnight. Next, 175 cubic centimeters of ethyl acetate was added while the reaction mixture was stirred. After all of the solids had dissolved, the reaction mixture was placed in a separatory funnel. When the reaction mixture had separated into two liquid phases, the bottom aqueous phase was drained off, reextracted with a further 100 cubic centimeters of ethyl acetate and the phases were separated. The two organic phases resulting from the two extractions were each allowed to stand over anhydrous magnesium sulfate in separate containers for several hours. Each extract was then separately filtered and stripped of solvent in a rotating evaporator over a warm water bath and under the vacuum provided by a water aspirator. The two crops of solids resulting from the stripping were each dried overnight in a convection oven at 50° C. to 55° C. The dried first crop weighed 75.4 grams while the dried second crop weighed 2.0 grams. The total yield was 80.9%, based on L-serine. Nuclear magnetic resonance spectroscopy showed traces of water to be present. Both crops were dried for an additional 18 hours over phosphorous pentoxide. Nuclear magnetic resonance spectroscopy after the additional drying did not detect any water. The spectra were in agreement with the standard spectrum for N-benzyloxycarbonyl-L-serine. The results of various analyses are shown in Table 10.

TABLE 10

| Analysis | First Crop | Second Crop |
|---|---|---|
| Assay by titration | | |
| Found: | 94.67%, 94.59% | 98.77%, 98.93% |
| Average Found: | 94.63% | 98.85% |
| Sodium Chloride | | |
| Found: | 0.19%, 0.19% | 0.19%, 0.18% |
| Average Found: | 0.19% | 0.19% |
| Water | | |
| Found: | 0.26%, 0.21%, 0.26% | 0.24%, 0.24% |
| Average Found: | 0.24% | 0.24% |
| Specific Rotation (0.4 gram/10 ml acetic acid) | | |
| Found: | +5.71°, +5.56° | Not Measured |
| Average Found: | +5.64° | |

The results, expressed as area percents, of liquid chromatography are shown in Table 11.

TABLE 11

| Compound | First Crop, Area Percent | Second Crop, Area Percent |
|---|---|---|
| N—benzyloxycarbonyl-L-serine | | |
| At 210 nm: | 97.7 | 97.3 |
| At 254 nm: | 99.7 | 99.3 |
| Benzyl Alcohol | | |
| At 210 nm: | 0.1 | 0.1 |
| At 254 nm: | 0.1 | 0.1 |
| Other | | |
| At 210 nm: | 2.3 | 2.7 |
| At 254 nm: | 0.3 | 0.7 |

EXAMPLE VII

This example shows the effect of using PEG-600 as a phase transfer catalyst in the preparation of N-benzyloxycarbonyl-L-serine.

A 1-liter, 5-necked reaction flask equipped as in Example I was charged with 52.55 grams of L-serine and 315 cubic centimeters of water. Forty grams of 50% aqueous sodium hydroxide solution was then added to convert the amino acid to the sodium salt. The reaction mixture then had a pH of about 10.6. To the reaction mixture was added 1.50 grams of PEG-600, followed by stirring for 5 minutes. The additions of 87.85 grams of benzylchloroformate ("BCF") and 40 grams of 50% aqueous sodium hydroxide solution ("caustic") as separate streams were accomplished according to Table 12.

TABLE 12

| Time, hours:minutes | Temperature, °C. | pH | Volume BCF in Addition Funnel, cm³, approximate | Volume Caustic in Addition Funnel, cm³, approximate | Remarks |
|---|---|---|---|---|---|
| 0:00 | 16 | 10.7 | 73 | 27 | BCF addition begun. |
| 0:03 | 16 | 10.65 | 69 | 27 | Reaction mixture became cloudy. pH drop began. |
| 0:06 | 17 | 10.59 | 66 | 27 | Began chilling vessel with ice bath. |
| 0:11 | 15 | 10.49 | 61 | 26.5 | Caustic addition begun. |
| 0:16 | 14 | 10.43 | 57 | 25 | Ice bath partially removed. |
| 0:21 | 15 | 10.42 | 53 | 23 | |
| 0:26 | 15 | 10.42 | 49 | 21 | |
| 0:31 | 14 | 10.44 | 44 | 19 | |
| 0:36 | 16 | 10.46 | 40 | 16 | Increased chilling. |
| 0:41 | 15 | 10.41 | 36 | 14 | |
| 0:46 | 16 | 10.47 | 32 | 12 | Increased chilling. |
| 0:51 | 15 | 10.41 | 29 | 11 | |
| 0:56 | 16 | 10.51 | 26 | 10 | Increased rate of BCF addition slightly. Increased chilling. |
| 1:01 | 14.5 | 10.48 | 23 | 8 | |
| 1:06 | 15.5 | 10.43 | 19 | 6 | |
| 1:11 | 15 | 10.42 | 14 | 4 | |
| 1:16 | 15 | 10.41 | 9 | 2.5 | |
| 1:21 | 16 | 10.46 | 5 | 1 | |
| 1:26 | 16 | 10.44 | 2 | 0.5 | |
| 1:28 | 16 | 10.43 | 0 | 0 | Both additions completed. |
| 1:29 | 16 | 10.4 | 0 | 0 | Added caustic dropwise to maintain pH >10.4 |
| 1:34 | 16 | 10.6 | 0 | 0 | Dropwise addition discontinued. pH is almost steady at 1:35. |
| 1:36 | 17 | 10.54 | 0 | 0 | pH is almost stable. Ice bath removed. |
| 1:46 | 18 | 10.5 | 0 | 0 | pH is almost stable. |
| 2:01 | 20 | 10.45 | 0 | 0 | pH is almost stable. Two drops of caustic were added; pH rose to 10.58. |
| 2:16 | 22 | 10.52 | 0 | 0 | One drop of caustic was added; pH rose to 10.59. |
| 2:46 | 24 | 10.43 | 0 | 0 | Two drops of caustic were added; pH rose to 10.56. |
| 4:11 | 24 | 10.39 | 0 | 0 | Two drops of caustic were added; pH rose to 10.6. |

Concentrated hydrochloric acid was charged to the addition funnel that had contained the benzylchloroformate. The reaction vessel was cooled with an ice bath until the temperature of the reaction mixture was about 12° C. and then the dropwise addition of concentrated hydrochloric acid was begun. When the pH reached about 5.0, a white precipitate began to form. The reaction mixture began thickening considerably when the pH reached about 4.8. When the pH reached about 4.7, the pH as indicated by the pH meter stopped decreasing although dropwise acid addition and cooling continued. It was noted that solid had precipitated out on the pH probe. The addition of 53 grams of water thinned the reaction mixture slightly, but the pH probe was still coated with solid which prevented an accurate pH reading. The pH probe was removed and washed thoroughly with distilled water to remove all adhering residues. Upon resubmerging the probe in the reaction mixture, however, it was quickly coated with solid which prevented accurate pH readings. After repeating the washing of the probe again without success (the meter indicated a pH of about 4.6), the acidification was followed with pH paper. At this point, the pH paper gave a reading of about 4. Acidification and cooling were continued and intermittent pH paper readings indicated values of 3, 3, somewhat less than 3, and suddenly about 1. At this point the pH meter suddenly indicated a value of about 0.8 and the pH probe began functioning again. The acidification was discontinued and a few cubic centimeters of caustic were added dropwise until a pH of about 1.6 was reached. The reaction mixture was stirred for about 30 minutes, after which the pH was about 1.8. The reaction mixture was stirred an additional 30 minutes and then 200 cubic centimeters of ethyl acetate was added, whereupon all solids dissolved. The reaction mixture was stirred for about 15 minutes and then charged into a one-liter separatory funnel where the phases were allowed to separate. The lower aqueous layer was drawn off and reextracted with 50 cubic centimeters of fresh ethyl acetate. After removal of the lower aqueous phase, the two organic phases were combined. The solvent was stripped in a Buchi rotating evaporator at an absolute pressure of about 10 kilopascals, using a water bath ultimately reaching about 45° C. The vacuum was released and the solids were scraped from the side of the flask. Once the solids were loosened and free flowing, evaporation was continued in the Buchi evaporator for about 2 hours at an absolute pressure of about 10 kilopascals and using a 45° C. water bath. The vacuum was released and the solids were placed in a drying dish. The solids were then dried for one hour and then overnight in a convection oven at about 47° C. The solids were pulverized and then dried for an additional 2 hours in the convection oven. The resulting product weighed 115.8 grams and represented a yield of 96.8%, based on L-serine. Analysis for purity was run by dissolving a sample of the product in water and titrating with a sodium hydroxide/methanol solution. Purity found: 98.43%, 97.91%. Average Purity Found: 98.17%. The product was analyzed for NaCl. Found: 0.36%, 0.38% NaCl. Average Found: 0.37% NaCl. The product was analyzed for moisture by the Karl Fischer method. Found: 0.50%, 0.28% $H_2O$. Average Found: 0.39% $H_2O$. Four-tenths of a gram of the product was dissolved in 10 milliliters of acetic acid and the specific rotation was determined. Found: +5.11°, +5.19°. Average Found: +5.15°. The product melted in the range of from 115° C. to 117° C. Liquid chromatography showed the product to contain 99.37 area percent N-benzyloxycarbonyl-L-serine when measured at 210 nanometers. When measured at 254 nanometers, liquid chromatography showed the product to contain 99.49 area percent N-benzyloxycarbonyl-L-serine. Nuclear magnetic resonance spectroscopy verified the structure of the product as that of N-benzyloxycarbonyl-L-serine.

This example shows about a 19½% increase in yield as compared to the yield of Example VI, and that PEG-600 effectively catalyzed the reaction.

EXAMPLE VIII

This example shows the effect of using PEG-900 as a phase transfer catalyst in the preparation of N-benzyloxycarbonyl-L-serine.

A 1-liter, 5-necked reaction flask equipped as in Example I was charged with 52.55 grams of L-serine and 265 cubic centimeters of water. Thirty grams of 50% aqueous sodium hydroxide solution was then added to convert the amino acid to the sodium salt. The reaction mixture then had a pH of about 9.62. To the reaction mixture was added 2.25 grams of PEG-900, followed by stirring for 5 minutes. The additions of 87.4 grams of benzylchloroformate ("BCF") and 50 grams of 50% aqueous sodium hydroxide solution ("caustic") as separate streams were accomplished according to Table 13.

Concentrated hydrochloric acid was charged to the addition funnel that had contained the benzylchloroformate. The reaction vessel was cooled with an ice bath until the temperature of the reaction mixture was about 12° C. and then concentrated hydrochloric acid was added dropwise over a period of about 20 minutes. When the pH reached about 5.1, the reaction mixture became quite thick as the pH was reduced to about 2.7. The pH probe became coated with white precipitate, causing the pH meter to fluctuate somewhat. Several times the probe was removed, washed with water and resubmerged in the reaction mixture. The pH was also ascertained with pH paper which indicated pH values between 2 and 3.

TABLE 13

| Time, hours:minutes | Temperature, °C. | pH | Volume BCF in Addition Funnel, $cm^3$, approximate | Volume Caustic in Addition Funnel, $cm^3$, approximate | Remarks |
|---|---|---|---|---|---|
| 0:00 | 15 | 9.64 | 73 | 33 | Both additions slowly begun. |
| 0:02 | 14 | 9.61 | 71 | 32.5 | Increased rate of BCF addition. |
| 0:07 | 14 | 9.7 | 66 | 32 | Began chilling vessel with ice bath. |
| 1:12 | 13 | 9.7 | 61 | 31 | Ice bath removed. |
| 0:22 | 14 | 9.7 | 50 | 27 | |
| 0:32 | 15 | 9.7 | 41 | 23 | |
| 0:37 | 17 | 9.75 | 36 | 18.5 | Began chilling vessel with ice bath. |
| 0:42 | 15 | 9.9 | 32 | 15 | |
| 0:47 | 14 | 9.7 | 28 | 14 | |
| 0:52 | 13 | 9.7 | 26 | 12 | |
| 0:57 | 13 | 9.8 | 22 | 10 | Ice bath partially removed. |
| 1:12 | 15 | 9.7 | 10 | 5 | |
| 1:17 | 14 | 9.6 | 5 | 2 | |
| 1:22 | 13 | 9.6 | 0 | 0 | Both additions completed. Ice bath removed. Added a few drops of caustic over a period of 6 minutes |
| 1:32 | 14 | 9.8 | 0 | 0 | pH had essentially stabilized. |
| 2:42 | 18 | 9.8 | 0 | 0 | |

Stirring was stopped and the solids were allowed to settle overnight. The next day the pH was still the same. Stirring was resumed and 200 cubic centimeters of ethyl acetate was added. No solids appeared to dissolve. Concentrated hydrochloric acid was added dropwise until a pH of about 1.5 was reached, whereupon much of the solids dissolved. The pH drifted up to about 1.9. A few drops of concentrated hydrochloric acid were added to lower the pH to 1.7 where it remained. All solids had dissolved. The reaction mixture was stirred rapidly for about 5 minutes and then charged to a one-liter separatory funnel where the phases were allowed to separate. The lower aqueous layer was drawn off and reextracted with 100 cubic centimeters of fresh ethyl acetate. After removal of the lower aqueous phase, the two organic phases were combined. The solvent was stripped in a Buchi rotating evaporator under the vacuum provided by a water aspirator (absolute pressure: about 7 to 10 kPa), using a water bath ultimately reaching about 50° C. The vacuum was released and the solids were scraped from the side of the flask. Once the solids were loosened and free flowing, evaporation was continued in the Buchi evaporator under vacuum for an hour. The vacuum was released and the solids were placed on a drying tray. The solids were then dried overnight in a convection oven at about 40° C. The temperature of the oven was raised to about 55° C. where the solids were further dried until the next day. The resulting product weighed 117.5 grams and represented a yield of 98.2%, based on L-serine. Analysis for purity was run by dissolving a sample of the product in water and titrating with a sodium hydroxide/methanol solution. Purity Found: 97.47%, 97.17%. Average Purity Found: 97.32%. The product was analyzed for NaCl. Found: 0.58%, 0.54% NaCl. Average Found: 0.56% NaCl. The product was analyzed for moisture by the Karl Fischer method. Found: 0.37%, 0.51% H$_2$O. Average Found: 0.44% H$_2$O. Four-tenths of a gram of the product was dissolved in 10 milliliters of acetic acid and the specific rotation was determined. Found: +4.90°, +4.18°. Average Found: +4.54°. The product melted in the range from 115° C. to 117° C. The product was analyzed for purity using liquid chromatography measured at 254 nanometers. Purity found: 100%(area), 100%(area). Average Purity Found: 100 area percent. The product was analyzed for purity using liquid chromatography measured at 210 nanometers. Purity Found: 96.96% (area), 96.63%(area). Average Purity Found: 96.80 area percent. The results of elemental analysis are shown in Table 14.

TABLE 14

|  | % C | % H | % N | % O |
|---|---|---|---|---|
| Found | 54.87 | 5.61 | 5.72 | 33.05 |
|  | 54.92 | 5.67 | 5.76 | 32.97 |
| Average Found | 54.90 | 5.64 | 5.79 | 33.01 |
| Theory | 55.23 | 5.48 | 5.86 | 33.44 |

The product was N-benzyloxycarbonyl-L-serine.

This example shows about a 21% increase in yield as compared to the yield of Example VI, and that PEG-900 effectively catalyzed the reaction.

Although the present invention has been described with reference to specific details of certain embodiments thereof, it is not intended that such details should be regarded as limitations upon the scope of the invention except insofar as they are included in the accompanying claims.

I claim:

1. In the method wherein alkali metal salt of an amino acid which is devoid of tertiary amino groups and quaternary ammonium groups, and which contains in addition to a primary amino group and at least one carboxylate anion, at least one functional group selected from the class consisting of hydroxyl, additional primary amino, secondary amino, primary imido, and primary amido, is reacted with benzylhaloformate selected from the class consisting of ring-substituted benzylchloroformate, ring-unsubstituted benzylchloroformate, ring-substituted benzylbromoformate, and ring-unsubstituted benzylbromoformate in a polyphase reaction mixture comprising an organic liquid phase and an aqueous liquid phase to produce alkali metal salt of an N-benzyloxycarbonyl amino acid in which the benzyl is substituted or unsubstituted and which contains said functional group, the improvement comprising conducting the reaction in the presence of a phase-transfer reagent comprising poly(oxyalkylene)glycol, polymer-supported poly(oxyalkylene)alcohol, or a mixture thereof.

2. The method of claim 1 wherein said phase-transfer reagent is represented by the formula

wherein
 a. R$_1$ is hydrogen or a polymeric substrate,
 b. one R of each individual —CH(R)CH(R)O— unit of said phase-transfer reagent is hydrogen or methyl, and the other R of said unit is hydrogen, methyl, or ethyl, and
 c. the average value of n is at least about 4.

3. The method of claim 2 wherein one R of each individual —CH(R)CH(R)O— unit of said phase-transfer reagent is hydrogen, and the other R of said unit is hydrogen or methyl.

4. The method of claim 2 wherein said phase transfer reagent is represented by the formula

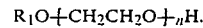

5. The method of claim 2 wherein R$_1$ is hydrogen.

6. The method of claim 2 wherein the average value of n is in the range of from about 4 to about 500.

7. The method of claim 2 wherein the average value of n is in the range of from about 4 to about 80.

8. The method of claim 2 wherein the average value of n is in the range of from about 5 to about 25.

9. The method of claim 1 wherein said phase-transfer reagent is represented by the formula

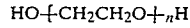

wherein the average value of n is in the range of from about 4 to about 80.

10. A method comprising
 a. reacting alkali metal salt of an amino acid which is devoid of tertiary amino groups and quaternary ammonium groups, and which contains in addition to a primary amino group and at least one carboxylate anion, at least one functional group selected from the class consisting of hydroxyl, additional primary amino, secondary amino, primary imido, and primary amido, with benzylhaloformate selected from the class consisting of ring-substituted benzylchloroformate, ring-unsubstituted benzylchloroformate, ring-substituted benzylbromoformate and ring-unsubstituted benzylbromoformate in a polyphase reaction mixture comprising an organic liquid phase and an aqueous liquid phase and in the presence of a phase-transfer reagent comprising poly(oxyalkylene)glycol, polymer-supported poly(oxyalkylene)alcohol, or a mixture thereof to produce alkali metal salt of an N-benzyloxycarbonyl amino acid in which the benzyl is substituted or unsubstituted; and b. acidifying said alkali metal salt of said N-benzyloxycarbonyl amino acid to produce N-benzyloxycarbonyl amino acid in which the benzyl is substituted or unsubstituted and which contains said functional group.

11. The method of claim 10 wherein said phase-transfer reagent is represented by the formula $$R_1O\text{---}\left[\text{---CH(R)CH(R)O---}\right]_n\text{---H}$$

wherein
a. $R_1$ is hydrogen or a polymeric substrate,
b. one R of each individual —CH(R)CH(R)O— unit of said phase-transfer reagent is hydrogen or methyl, and the other R of said unit is hydrogen, methyl, or ethyl, and
c. the average value of n is at least about 4.

12. The method of claim 10 wherein said phase-transfer reagent is represented by the formula $$R_1O\text{---}(CH_2CH_2O)_n\text{---}H$$

wherein $R_1$ is hydrogen or a polymeric substrate, and the average value of n is at least about 4.

13. The method of claim 12 wherein $R_1$ is hydrogen and the average value of n is in the range of from about 4 to about 80.

14. The method of claim 10 wherein said benzylhaloformate is ring-unsubstituted benzylchloroformate.

15. The method of claim 10 wherein said functional group is hydroxyl.

16. The method of claim 10 wherein said alkali metal salt of an amino acid which is reacted with said benzylhaloformate is alkali metal salt of threonine or alkali metal salt of serine.

17. The method of claim 10 wherein the pH of the aqueous liquid phase is maintained in the range of from about $pK_2'$ to about $(pK_2'+1.5)$ during the reaction of said alkali metal salt of said amino acid and said benzylhaloformate, where $pK_2'$ is the $pK_2'$ value of the amino acid whose alkali metal salt is employed as a reactant.

18. The method of claim 10 wherein the pH of the aqueous liquid phase is maintained in the range of from about $pK_2'$ to about $(pK_2'+1)$ during the reaction of said alkali metal salt of said amino acid and said benzylhaloformate, where $pK_2'$ is the $pK_2'$ value of the amino acid whose alkali metal salt is employed as a reactant.

19. The method of claim 10 wherein said alkali metal is lithium, sodium, or potassium.

20. The method of claim 10 wherein said alkali metal is sodium.

21. The method of claim 10 wherein the reaction of said alkali metal salt of an amino acid and said benzylhaloformate is conducted at temperatures in the range of from about $-10°$ C. to about $+60°$ C.

22. The method of claim 10 wherein the final pH of the reaction mixture resulting from said acidification is in the range of from about 1 to about 4.

23. The method of claim 10 wherein said acidification is conducted using hydrochloric acid.

24. The method of claim 10 wherein sodium or potassium salt of an amino acid which is devoid of tertiary amino groups and quaternary ammonium groups, and which contains a hydroxyl group is reacted with benzylchloroformate in a polyphase reaction mixture and in the presence of phase-transfer reagent represented by the formula $$HO\text{---}(CH_2CH_2O)_n\text{---}H$$

wherein the average value of n is in the range of from about 4 to about 80 to produce sodium or potassium salt of benzyloxycarbonyl amino acid; and wherein said sodium or potassium salt of said benzyloxycarbonyl amino acid is acidified with hydrochloric acid to produce N-benzyloxycarbonyl amino acid containing a hydroxyl group.

* * * * *